United States Patent
Kerr et al.

(10) Patent No.: US 12,007,386 B2
(45) Date of Patent: Jun. 11, 2024

(54) RESPIRATORY SIMULATION SYSTEM INCLUDING AN ANATOMICAL MODEL OF THE HUMAN NASAL CAVITY CONFIGURED FOR IN VITRO INHALATION STUDIES AND ASSOCIATED METHODS

(71) Applicant: Government of the United States (Air Force), Wright-Patterson AFB, OH (US)

(72) Inventors: Lei L. Kerr, Oxford, OH (US); Saber M. Hussain, Beavercreek, OH (US); Andrew Yerich, Oxford, OH (US)

(73) Assignee: Miami University and Government of the United States (Air Force)

( * ) Notice: Subject to any disclaimer, the term of this patent is extended or adjusted under 35 U.S.C. 154(b) by 695 days.

(21) Appl. No.: 16/680,851

(22) Filed: Nov. 12, 2019

(65) Prior Publication Data
US 2020/0150110 A1    May 14, 2020

Related U.S. Application Data

(60) Provisional application No. 62/760,901, filed on Nov. 13, 2018.

(51) Int. Cl.
| | |
|---|---|
| G01N 33/50 | (2006.01) |
| B29C 33/38 | (2006.01) |
| B29C 39/02 | (2006.01) |
| B29C 64/386 | (2017.01) |
| B33Y 10/00 | (2015.01) |
| B33Y 50/00 | (2015.01) |
| B33Y 80/00 | (2015.01) |
| C12N 5/071 | (2010.01) |
| G09B 23/30 | (2006.01) |
| G09B 23/34 | (2006.01) |
| B29L 31/40 | (2006.01) |

(52) U.S. Cl.
CPC ..... *G01N 33/5082* (2013.01); *B29C 33/3835* (2013.01); *B29C 33/3842* (2013.01); *B29C 39/02* (2013.01); *B29C 64/386* (2017.08); *B33Y 10/00* (2014.12); *B33Y 50/00* (2014.12); *B33Y 80/00* (2014.12); *C12N 5/0688* (2013.01); *G09B 23/30* (2013.01); *G09B 23/303* (2013.01); *G09B 23/34* (2013.01); *B29L 2031/40* (2013.01); *C12N 2513/00* (2013.01); *C12N 2533/00* (2013.01); *C12N 2533/90* (2013.01)

(58) Field of Classification Search
None
See application file for complete search history.

(56) References Cited

U.S. PATENT DOCUMENTS

| | | | | |
|---|---|---|---|---|
| 2012/0085344 A1* | 4/2012 | Luber | ............... | A61M 15/0085 128/203.29 |
| 2020/0046919 A1* | 2/2020 | Smyth | ............... | A61K 31/4184 |

OTHER PUBLICATIONS

Lechanteur, Anna et al. The role of mucus in cell-based models used to screen mucosal drug delivery. Advanced Drug Delivery Reviews 124 (2018) 50-63. (Year: 2018).*
Staymates, M. E. et al., Biomimetic Sniffing Improves the Detection Performance of a 3D Printed Nose of a Dog and a Commercial Trace Vapor Detector, Scientific Reports, Dec. 1, 2016, pp. 1-10, 6:36876, Springer Nature, United States.

* cited by examiner

*Primary Examiner* — Nghi V Nguyen
(74) *Attorney, Agent, or Firm* — Jason H. Foster; Kremblas & Foster

(57) ABSTRACT

The anatomical model of a nasal cavity, such as a human nasal cavity, for in-vitro inhalation studies such as toxicological screening, intranasal drug delivery studies, and neurophysiological studies. The model includes a model body including separable upper and lower model portions together defining the nasal cavity and including fluidic channels therein that define an olfactory region of the upper model portion, and a nasal passage defined in the lower model portion. A biocompatible porous membrane is positioned between the upper and lower model portions, and the biocompatible membrane is configured for culturing olfactory epithelium cells thereon. An artificial mucous layer coats a surface of the nasal cavity and is configured to collect particles passing through the nasal cavity.

10 Claims, 4 Drawing Sheets

RESPIRATORY SIMULATION SYSTEM INCLUDING AN ANATOMICAL MODEL OF THE HUMAN NASAL CAVITY CONFIGURED FOR IN VITRO INHALATION STUDIES AND ASSOCIATED METHODS

CROSS-REFERENCES TO RELATED APPLICATIONS

This application claims the benefit of U.S. Provisional Application No. 62/760,901 filed Nov. 13, 2018. This prior application is hereby incorporated by reference.

STATEMENT REGARDING FEDERALLY-SPONSORED RESEARCH AND DEVELOPMENT

The invention described herein may be manufactured and used by or for the Government of the United States for all governmental purposes without the payment of any royalty.

THE NAMES OF THE PARTIES TO A JOINT RESEARCH AGREEMENT (Not Applicable)

REFERENCE TO AN APPENDIX (Not Applicable)

BACKGROUND OF THE INVENTION

The present invention relates generally to inhalation studies. More specifically, this invention pertains to in-vitro inhalation toxicological screening, intranasal drug delivery studies and/or neurophysiological studies using an anatomical model of a nasal cavity (e.g. a human nasal cavity).

Figure 1:
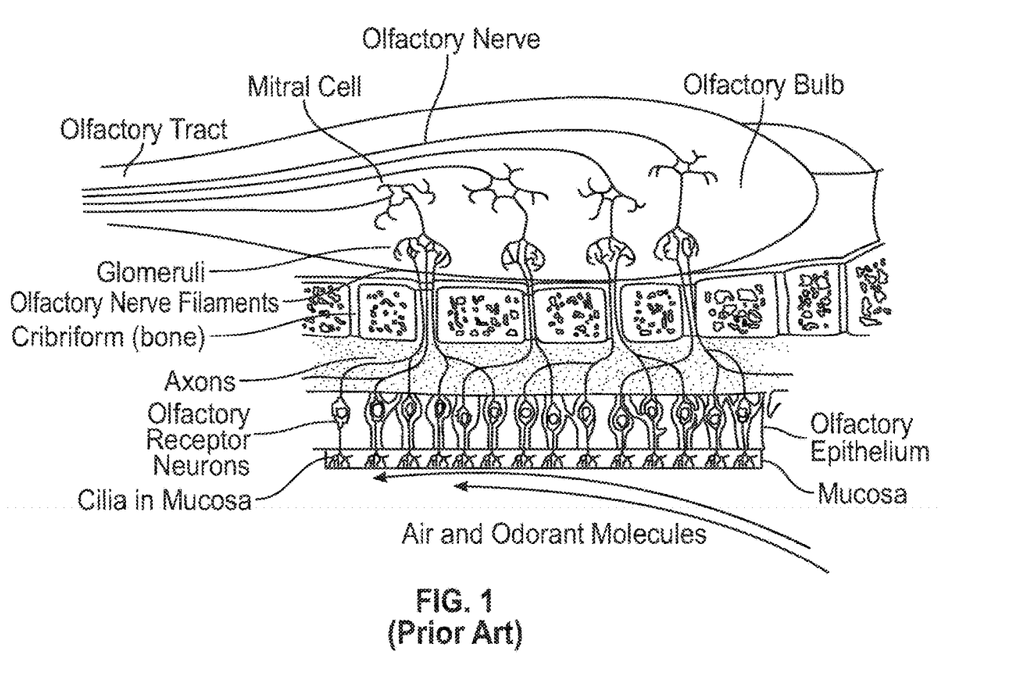
FIG. 1 is a prior art schematic diagram illustrating the human olfaction system.

Nanomaterials (NM) can bypass the blood brain barrier (BBB), enter the olfactory mucosa and translocate anterogradely via the axons of the olfactory nerve to the brain and further impair cellular components in the brain. As seen from FIG. 1, the olfactory nerves start from the olfactory mucosa and travel to the olfactory tract until it reaches the olfactory bulb. The neurotoxicity is a function of NM dose. The olfactory epithelium/mucus is the first and only part of the central nerve system (CNS) that is exposed directly to the environment when NM are inhaled. Thus, quantifying the NM deposition in the olfactory epithelium/mucus will provide an accurate prediction of neurotoxicity of NM. Some toxicology studies use exceptionally high concentrations of nanoparticles in order to illicit a clear toxic response and often times, real-world exposure concentrations are not considered when developing experimental parameters.

There may be a need for an approach to systematically assess the deposition of vast variety of NM with different toxicokinetics (e.g. effects of nanoparticle size, surface chemistry, shape, crystal structure, etc.) in the nasal olfactory region via the nose-brain transport and thus to provide a basis for accurate prediction of the NM neurotoxicity and the induced brain diseases.

Current state-of-art in-vivo, in-vitro and in-silico neurotoxicity research does not satisfy this need. The in-vivo investigations use animals to be exposed to NM. Due to the sacrifice of animals, only limited materials and inhalation conditions are studied. In addition, the human nose has a very distinct geometry to that of animals, and this must be taken into consideration. The in-vitro model provides an alternative route for risk assessment, but none of the current state-of-art in-vitro research appears to perform the studies on the NM deposition in the olfactory region.

In-silico studies of NM deposition in the olfactory region may use computational fluid dynamics (CFD) to study air flow velocities, aerosol concentrations, regional particle deposition (e.g. olfactory region), etc. inside the nasal cavity using the numerical models governed by the continuity and Navier-Stokes transport equations. There are limitations of CFD modeling in nasal airflow that may be attributable to the various researcher-dependent assumptions made about boundary conditions, flow patterns, and methods of solving general flow equations, etc. The omission of the mucus layer is another drawback of CFD modeling. The mucus layer traps incoming particles and has significant influence on nasal airflow and particle deposition.

Therefore, neglecting to account for the effect of mucus and olfactory epithelium on nasal flow affects the accurate prediction of particle deposition in the nasal olfactory region.

This background information is provided to reveal information believed by the applicant to be of possible relevance to the present invention. No admission is necessarily intended, nor should be construed, that any of the preceding information constitutes prior art against the present invention.

BRIEF SUMMARY OF THE INVENTION

With the above in mind, embodiments of the present invention are related to a system, model and methods that are developed to simulate human inhalation toxicological screening or intranasal drug delivery of chemicals or materials. The embodiments include the use of fluidic channels (e.g. defined by a microfluidic system or biomaterial framework) mimicking the human olfactory region in an artificial nasal cavity that allows the growth of olfactory neuron and/or epithelium cells. The anatomically correct human nasal cavity with the incorporation of human mucus plus neuron and/or epithelial cells allows the mimicking of real air flow to the human olfactory region via the nose.

An embodiment of the present invention is directed to an anatomical model of a nasal cavity (e.g. a human nasal cavity) for at least one of in-vitro inhalation toxicological screening, intranasal drug delivery studies, and neurophysiological studies. The model includes a model body including separable upper and lower model portions together defining the nasal cavity and including fluidic channels therein that define an olfactory region of the upper model portion, and a nostril region defined in the lower model portion. A biocompatible porous membrane is positioned between the upper and lower model portions. The biocompatible membrane is configured for culturing olfactory epithelium cells thereon. An artificial mucous layer coats a surface of the nasal cavity and is configured to collect particles passing through the nasal cavity.

Additionally, and/or alternatively, the artificial mucous layer is configured to be removed upon separation of the upper and lower model portions.

Additionally, and/or alternatively, the upper and lower model portions comprise a silicone material.

Additionally, and/or alternatively, the biocompatible porous membrane includes artificial pores defining the permeability of the biocompatible porous membrane. The pores may mimic the human olfactory region.

Additionally, and/or alternatively, a microfluidic system and/or a biomaterial framework defines the fluidic channels and is configured for the growth of olfactory neuron and epithelium cells.

Additionally, and/or alternatively, a breathing system is coupled to the model body and configured to simulate a breathing pattern with air entering and exiting via the nostril region. The combination of features defines a respiratory simulation system.

An embodiment is directed to a method of in-vitro inhalation toxicological screening. The method comprises: providing an anatomical model of a nasal cavity comprising a model body including separable upper and lower model portions together defining the nasal cavity and including fluidic channels therein that define an olfactory region of the upper model portion and define a nostril region of the lower model portion; positioning a biocompatible porous membrane between the upper and lower model portions; culturing olfactory neuron cells within the fluidic channels; culturing olfactory epithelium cells on the biocompatible porous membrane; coating a surface of the nasal cavity with an artificial mucous layer; coupling a respiratory simulation system to the anatomical model of the nasal cavity and simulating a breathing pattern with air entering and exiting via the nostril region; and sampling at least some of the artificial mucous layer to determine concentrations and distributions of chemical substances therein.

Additionally, and/or alternatively, the method includes forming artificial pores in the biocompatible porous membrane to define the permeability of the biocompatible porous membrane.

Additionally, and/or alternatively, sampling comprises separating the upper and lower model portions to access the artificial mucous layer. Sampling may further comprise removing at least some of the artificial mucous layer.

Additionally, and/or alternatively, the upper and lower model portions comprise a silicone material.

Additionally, and/or alternatively, the method includes creating a microfluidic system and/or a biomaterial framework that defines the fluidic channels and is configured for the growth of olfactory neuron and epithelium cells.

Embodiments are also directed to a method of making an anatomical model of a nasal cavity for at least one of in-vitro inhalation toxicological screening, intranasal drug delivery studies, and neurophysiological studies, the method comprising: molding an elastomer material around a cast of a nasal cavity to define a model body; removing the cast from the model body to define a nasal cavity therein including fluidic channels; dividing the model body into upper and lower model portions that together define the nasal cavity including the fluidic channels therein that define an olfactory region of the upper model portion and define a nostril region of the lower model portion; positioning a biocompatible porous membrane on the upper model portion adjacent the olfactory region; aligning the upper and lower model portions together with the biocompatible porous membrane therebetween; culturing olfactory neuron cells within the fluidic channels; culturing olfactory epithelium cells on the biocompatible porous membrane; and coating the nasal cavity with an artificial mucous layer configured to collect particles passing through the nasal cavity.

Additionally, and/or alternatively, creating the cast of the nasal cavity includes: obtaining a digital image of a patient's nasal cavity; forming a 3D digital model based upon the digital image; and 3D printing the cast of the nasal cavity based upon the 3D digital model.

Additionally, and/or alternatively, the method includes forming artificial pores in the biocompatible porous membrane to define the permeability of the biocompatible porous membrane.

Additionally, and/or alternatively, the method includes creating a microfluidic system and/or biomaterial framework that defines the fluidic channels of the nasal cavity and is configured for the growth of olfactory neuron and epithelium cells.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or terms similar thereto are often used. They are not limited to direct connection, but include connection through other elements where such connection is recognized as being equivalent by those skilled in the art.

DETAILED DESCRIPTION OF THE INVENTION

U.S. Provisional Application No. 62/760,901 filed Nov. 13, 2018, which is the above-claimed priority application, is incorporated in this application by reference.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure Like numbers refer to like elements throughout.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

The present invention is directed to a system, model and methods that are developed to simulate human inhalation toxicological screening or drug delivery of chemicals or materials. This approach includes fluidic channels (e.g. microfluidic system or scaffold biomaterials) mimicking the olfactory region in an artificial nasal cavity that allows the growth of olfactory neuron and epithelium cells. The anatomically correct human nasal cavity with the incorporation of human mucus plus neuron or epithelial cells allows the mimicking of realistic air flow to the human olfactory region via the nose.

The embodiments may provide versatile applications in many fields such as toxicology and medicine. The approach may eliminate the use of animals by developing an innovative respiratory device to meet the current need for an accurate in-vitro tool to study the NM deposition in the nose olfactory region which is an important first step in determining the NM dosimetry on neurotoxicity. In-vivo experimentation may be the preferred physiologically realistic way of measuring NM deposition in the nasal olfactory region.

However, with current techniques, because the animals must be sacrificed, only a very limited number of experiments can be run in these in-vivo studies. This constraint makes it nearly impossible to conduct studies that must account for large numbers of permutations.

For example, NMs are purposely engineered with varying geometries, morphologies, and surface chemistries in order to exhibit the tunable physical properties. It would be too expensive, too time-consuming, and too labor-intensive to perform in-vivo studies of each permutation. In addition, animals such as rats, mice and squirrels have nasal geometries that are distinctly different from humans, requiring additional precautions and measures to predict the NM deposition in the nose olfactory region. Thus, important systematic kinetic information, such as dose levels, ventilation conditions, inhalation rates, breathing patterns (e.g., healthy vs. asthmatic patient) and nasal geometry (e.g., children vs. adults) is difficult to gather from the animal models. Because of these restrictions, in vivo studies have been decreasing.

Figure 2A:
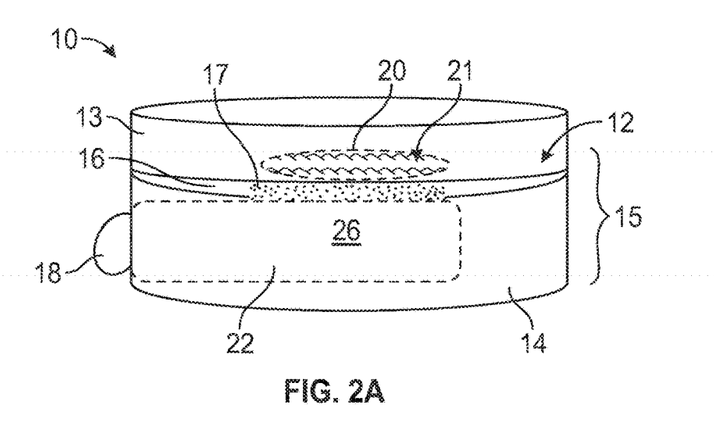
FIG. 2A is a schematic diagram illustrating an anatomical model of a nasal cavity according to an embodiment of the present invention.
Figure 2B:
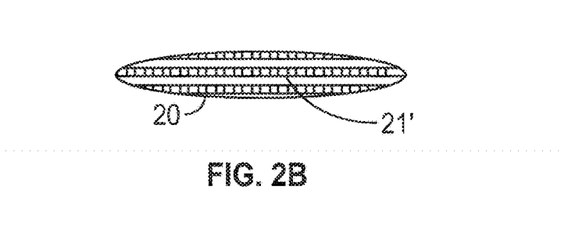
FIG. 2B is a schematic diagram illustrating another embodiment of the olfactory region of the anatomical model of the nasal cavity of FIG. 2A.

Referring now to FIGS. 2A and 2B, an anatomical model 10 according to an embodiment of the present invention will now be discussed in greater detail. FIG. 2A is a schematic diagram of an embodiment of the anatomical model 10 of a nasal cavity 15. FIG. 2B is a schematic diagram of another embodiment of the olfactory region 20 of the anatomical model 10 of the nasal cavity 15 of FIG. 2A.

The anatomical model 10 of a nasal cavity (e.g. a human nasal cavity) is for in-vitro inhalation studies including toxicological screening, intranasal drug delivery studies, and/or neurophysiological studies, for example. The model 10 includes a model body 12 including an upper model portion 13 and a lower model portion 14 that are separable. Together the portions 13 and 14 define the nasal cavity 15 and include fluidic channels 21 therein that define an olfactory region 20 of the upper model portion 13, and a nasal passage 22 defined in the lower model portion 14. A biocompatible porous membrane 16 is positioned between the upper and lower model portions 13 and 14. The biocompatible porous membrane 16 is configured for culturing olfactory epithelium cells thereon. An artificial mucous layer 26, which may be a high-viscosity fluid, coats a surface of the nasal cavity 15 and is configured to collect particles passing through the nasal cavity. The mucous layer 26 may coat a limited portion of the surface of the nasal cavity 15, or may coat most or all of the surfaces of the nasal cavity 15. The artificial mucous layer 26 is configured to be removed after separation of the upper and lower model portions 13 and 14. A nostril structure such as a nose or nasal vestibule/septum 18 may be included. Furthermore, artificial nose hair can be added.

As shown in FIG. 2A, a microfluidic system defines the fluidic channels 21 and is configured for the growth of olfactory neuron and epithelium cells. FIG. 2B shows an alternative embodiment with a biomaterial framework or scaffolding defining the fluidic channels 21'.

With additional reference to FIG. 3, an embodiment of a method of making the anatomical model 10 of FIG. 2A will be described. The method includes creating a cast of the nasal cavity by obtaining 31 a digital image of a patient's nasal cavity, forming 32 and 33 a 3D digital model based upon the digital image, and 3D printing 34 and 35 the cast of the nasal cavity based upon the 3D digital model. The method includes molding 36 and 37 an elastomer material around the cast of the nasal cavity to define a model body 10 and then removing the cast from the model body 10 to define a nasal cavity 15 therein including fluidic channels 21. The model body 10 is divided into upper and lower model portions 13 and 14. Together these portions 13 and 14 define the nasal cavity 15 including the fluidic channels 21 therein that define an olfactory region 20 of the upper model portion 13 and define a nostril region 22 of the lower model portion 14.

The cast of the nasal cavity may be made of wax or another material that melts at a temperature lower than the melting temperature of the elastomer material that is molded around it. The upper and lower model portions 13 and 14 may be formed from a silicone material, such as Polydimethylsiloxane (PDMS).

The biocompatible porous membrane 16 is positioned on the upper model portion 13 adjacent the olfactory region 20. The upper and lower model portions 13 and 14 are aligned together with the biocompatible porous membrane 16 therebetween. The method includes culturing olfactory neuron cells within the fluidic channels 21; culturing olfactory epithelium cells on the biocompatible porous membrane 16; and coating the nasal cavity 15 with an artificial mucous layer 26 configured to collect particles passing through the nasal cavity. The biocompatible porous membrane 16 may include artificial pores 17 defining the permeability of the biocompatible porous membrane. Thus, artificial pores 17 may be formed in the biocompatible porous membrane 16 to define the permeability of the biocompatible porous membrane.

Figure 3:
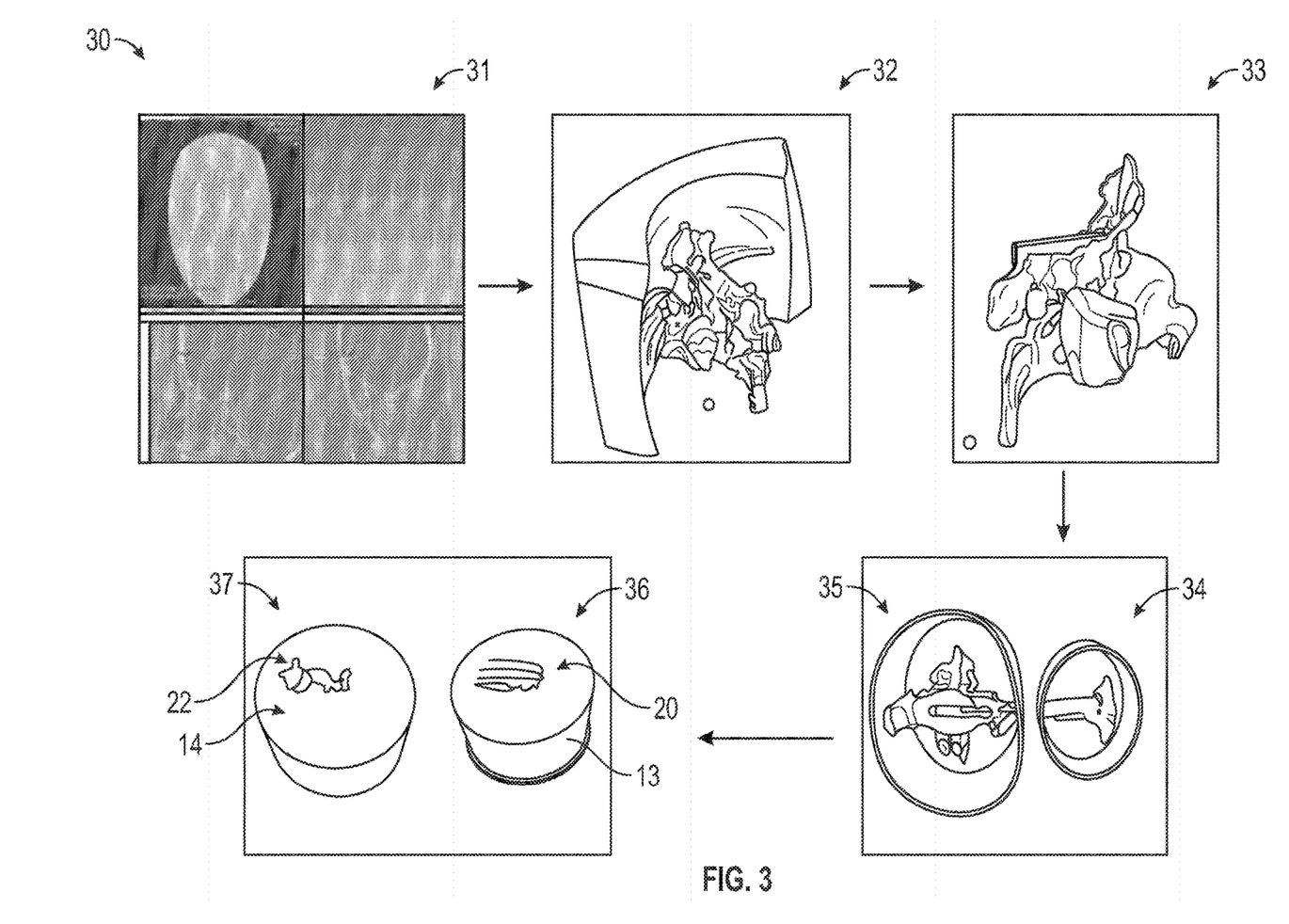
FIG. 3 is a flow chart illustrating steps in an embodiment of a method of making the anatomical model of FIG. 2A.

As an example, the manufacturing process is for the creation of a 3D printed nasal cavity with integrated microfluidic channels 21 in the olfactory region 20 and may include the use of the steps shown in FIG. 3, such as 31) a CT scan; 32) an initial 3D cast; 33) post alteration and integration of microfluidic channel 3D cast; 34) the bottom of a 3D printed mold; 35) the top of a 3D printed mold; 36) the upper portion 13 of the PDMS cured model including the olfactory region 20; and 37) the lower portion 14 of the PDMS cured model including the nostril region 22.

Microfluidic channels 21 are fabricated and integrated to the nasal structure using a negative 3D printing method, for example. The microfluidic channel structure is added to the approximate location of the olfactory region 20 that allows for various olfactory neuron cells to be cultured at a location separated from the nasal passage 22 by the membrane 16. The integrated system of microfluidic channels 21 in the nasal cavity can also be achieved by methods other than those described herein, as will be apparent to a person of ordinary skill.

The membrane 16 is overlapped over the olfactory region 20 and fixated to the upper mold portion 13 through the use of uncured PDMS, for example. Once cured, this PDMS acts as an adhesive fusing the membrane 16 to the model 10. The microfluidic channels 21 are aligned and separated by the middle flexible, porous PDMS membrane 16, e.g. of 60 μm thickness, to represent the human olfactory epithelium layer thickness. The olfactory epithelium cells will be cultured on the porous membrane 16.

The example of the present approach puts a mucus coating 26 in a nose model 10 that can be opened. Thus, any drug/particles passing through nose model during testing will be entrapped in the mucus coating which can later be removed for mass analysis. Through this approach, the drug/particle deposition distribution can be determined in each region of the cavity 15, including the olfactory region 20, which is one of the most important regions regarding drug/particle translocation to the brain. A fluid is placed inside the olfactory chamber, and this fluid may be phosphate-buffered saline (PBS) solution, cell culture media or another suitable fluid.

Further details of an example embodiment will be described. For 3D model creation, a patient specific CT scan may be obtained. The program "3D Slicer" is able to load DICOM files for viewing and manipulation, specifically with 3D modeling and printing purposes in mind. The obtained CT scan is loaded into the program and the nasal cavity space is able to be selected and sectioned off from all other portions. A 3D model may be created from the selected portions and exported as an appropriate file format for additional model manipulation, e.g. stereolithography (STL).

For model manipulation, the created model may be imported into the computer program "Autodesk Mesh" and all imperfections and holes within the model may be smoothed out, filled, and any disconnects deleted. In the creation of this model, the ear cavities may also be filled, and these large portions removed in order to give the model a leaner look and to reduce the amount of volume that would be 3D printed later. A rectangular portion created in the program "Autodesk Inventor" was created to serve as the upper channel and placed in the approximate location of the olfactory. With the model finished, the device may be 3D printed by a Solid Scape 3Z Pro Printer at a 100% fill density and a resolution of 0.10 mm layer height using Solid Scape 3Z Modeling Wax and Solid Scape 3Z Support Wax. Once the model is done printing, the supporting material may be removed through the use of a heated solvent.

For the molding process, a PDMS solution may be created by mixing 184 Silicone Elastomer Base and 184 Silicone Elastomer Curing Agent in a 10:1 mass ratio. The PDMS is degassed and poured into a container with, for example, a human head shape holding the previously created nasal cavity mold. The mold is placed in an oven at 70° C. for 1.5 hours in order for the PDMS to cure completely. Upon curing, the container is removed and allowed to cool. Once at room temperature, the container is cut off the cured PDMS using a scalpel. The PDMS product is then placed in the oven at 150° C. to allow the modeling wax mold to melt for approximately 2 hours. Upon completion, a PDMS device mimicking the nasal cavity 15 with the inclusion of microfluidic channels 21 is created.

In order to include a PDMS membrane in the 3D printed nose model to create an integrated microfluidic channel structure for mimicking olfactory region, the nasal cavity may be split into two halves. For alignment purposes, each half may be designed to have a pair of notches, for example, extending on the top half and caving in on the bottom half. These notches occur at the same location for both halves, and in turn when both halves are aligned appropriately, the notches will lock into each other, and therefore keep the two halves aligned correctly to create the full nasal cavity device.

Having clear access to the channels 21 allows for the membrane 16 to be placed flat on the surface, dividing the olfactory region 20 from the rest of the nasal passage 22 when fully assembled. The microfluidic PDMS membrane 16 may be created by spin-coating PDMS solution onto silicon wafers at 180 RPM. This spin coating method may be a more time efficient and simpler method than the traditional photolithography for membrane production. Once cured, the membrane 16 may be penetrated with a micro-needle stamping device to create artificial pores 17 to thereby adjust the membrane's permeability to the physiological $O_2$ permeability through the cell membrane. There may be five artificial pores 17 in an exemplary membrane 16, or there may be more or fewer than five pores 17.

PDMS has acceptable biocompatibility and has been widely used in medical plants, biomedical devices and cell biology. Various mammalian cells and lung epithelium cells have been demonstrated to grow on PDMS. The membrane pore size, thickness and channel dimension on the cell growth and biocompatibility may be selected as needed. The PDMS membrane 16 can be UV or collagen or other surface treatment methods treated to change its hydrophobic behavior to hydrophilic which may allow the researcher to adjust for needed transport properties and cell culture.

One of the limitations of nasal cast models reported in the literature is that they give information only about overall drug/particle deposition in the model as a whole and are not capable of determining the distribution (e.g. olfactory area) of NM within the cavity. The present approach puts a mucus coating 26 in a nose model 10 that can be opened, so that the drug/particles entrapped in the mucus coating can be removed for mass analysis. Examples of materials the mucus layer 26 can be created from include a solution of Polyox WSR Coagulant with water. This may be applied inside the nose cavity 15 when the nose model is opened, for example.

Figure 4:
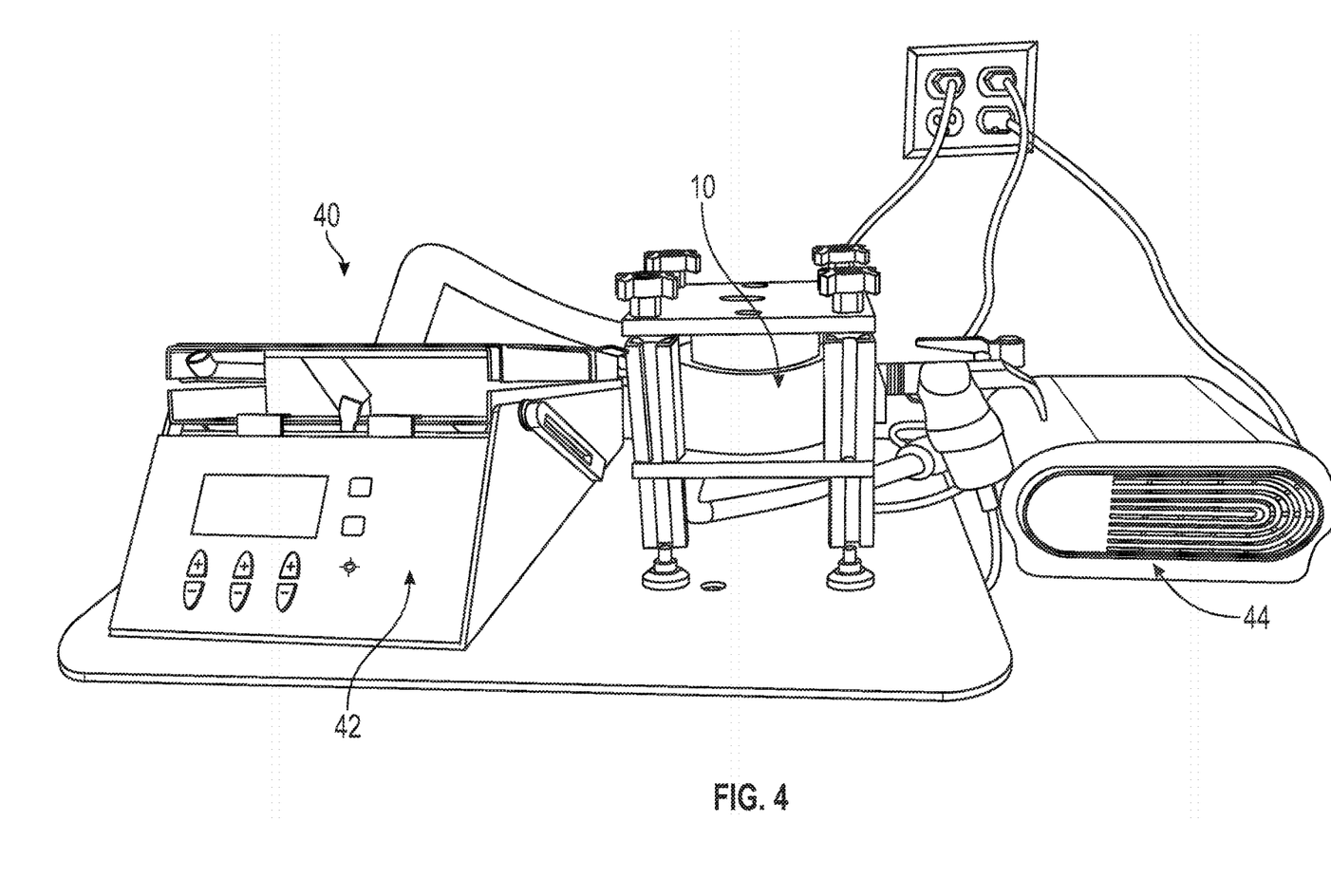
FIG. 4 is a schematic diagram illustrating a respiratory simulation system that includes a breathing system and the anatomical model of FIG. 2A.

FIG. 4 shows an experimental setup of an integrated respiratory device 40. The integrated respiratory system 40 may be used both in a laboratory environment and in a field environment. An artificial lung device 42, known by the registered trademark QuickLung® Breather, is connected to the artificial cavity via a series of tubes entering the model's pharynx region. Once the tube has been inserted into an exit point in the model 10, the tubing may be surrounded by a molding putty or secured by any securing device, creating an air tight seal. When the Breather is active, realistic air flow mimicking that of an actual lung is generated through the nasal cavity. When the connection between the artificial lung and the nasal model is properly sealed, the air can only enter and exit through the model's nostrils. This accurately simulates an actual breathing process. Different inspiratory flow rates/breathing patterns can be delivered, such as normal breathing, apnea related breathing, and shallow breathing. In the lab environment, e.g. for testing nanoparticle toxicity or intranasal drug screening studies, an optional nebulizer 44 or aerosol generator may be connected to the nostril of the nasal model. This device design also allows a quick add-on of an SMPS/CPC system through a tee in the flow circuit. The system 40 may be portable, e.g., for a field NM exposure study.

Figure 5:
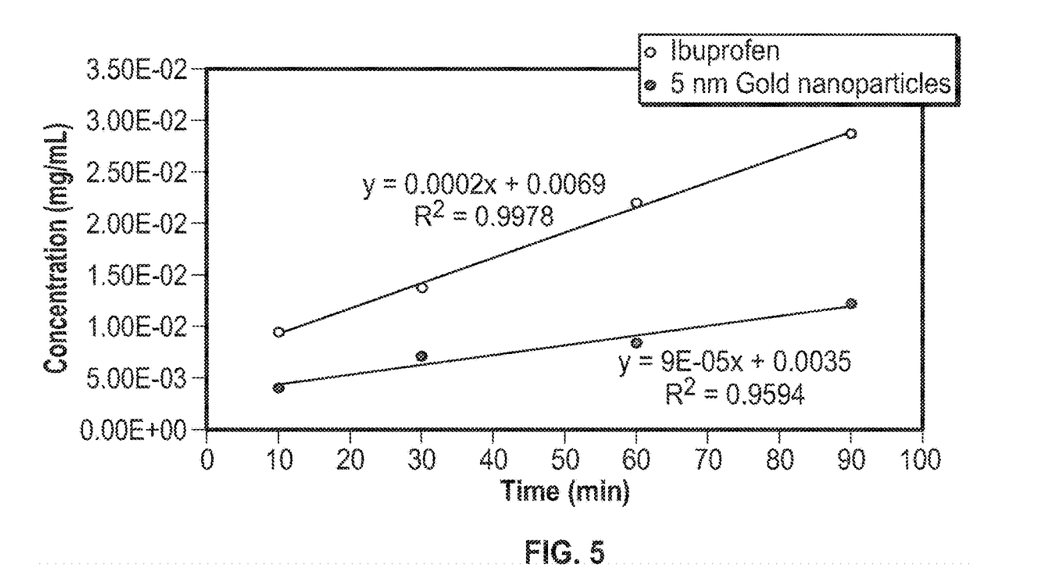
FIG. 5 is a graph showing the concentration of the fluid in the olfactory region over the course of exposure to ibuprofen and 5 nm gold nanoparticles.

To demonstrate the prototype use of this device, a transport study on Ibuprofen and gold (Au) nanoparticles was performed. The artificial nasal cavity device was exposed to a nebulizer filled with either powdered ibuprofen dissolved in phosphate buffered saline or 5 nm gold nanoparticles in distilled water. After exposure, the fluid located in the olfactory chamber of the device was withdrawn via a syringe and transferred for UV spectroscopy. Comparing absorption values to previously obtained calibration curves, the concentration of particles that diffused into the olfactory portion of the nasal cavity was able to be determined, along with the percentage of saturation that had been reached, as shown in FIG. 5. All PDMS membranes used in the device had puncture openings to permit diffusion. Longer duration exposures showed a linear increase in the amount transported to the olfactory region, with ibuprofen transporting more efficiently than that of the 5 nm gold nanoparticles.

Figure 6:
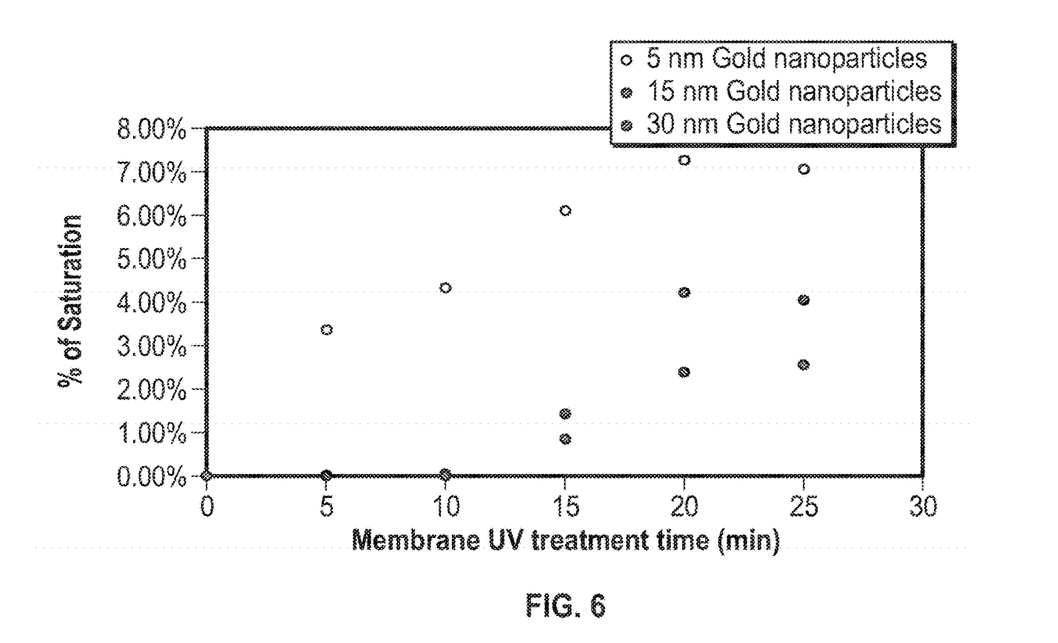
FIG. 6 is a graph showing the percentage of saturation reached of the fluid in the olfactory region after 10 minutes of exposure to varying sizes of gold nanoparticles with dividing membranes receiving varying amounts of UV treatment.

With reference to the graph of FIG. 6, four additional sizes (5, 15, 30 and 50 nm) of gold nanoparticles as well as PDMS crosslink time were tested on the artificial nasal cavity device. All nanoparticles were dissolved in distilled water and exposed to the device for 10 minutes using a nebulizer. The amount transported to the olfactory region was calculated and determined through the use of UV spectroscopy. Comparing the amount transported of the different sizes, the smaller the particle, the more transportation occurred, with no transportation occurring for the 50 nm particles. In addition to having less transport, bigger nanoparticles also did not begin to transport immediately after crosslinking the membranes. While the 5 nm particles transported after only 5 minutes of UV treatment, the 15 and 30 nm did not begin to transport until after 10 and 15 minutes respectively. This trend follows literature simulation which has found that smaller particles deposit more effectively in the olfactory region than their larger counterparts.

The application of the proposed embodiments is not limited to neurotoxicity study and NMs. It will also benefit the regenerative neural medicine community by providing a tool to perform the brain drug screening and study the brain drug delivery mechanism. In the past decades, the community has a rapid growing interest on delivering therapeutic agents to the brain and spinal cord for treating Alzheimer's disease, stroke, Parkinson's, head injury, spinal cord injury, depression, anxiety, and other CNS disorders by the practical and noninvasive intranasal delivery method of bypassing the BBB. The embodiments may have the capability to assess versatile NMs with different properties and assess variable environmental conditions (e.g. humidity, temperature, altitude, ventilation speed, etc.). Humans with different breathing patterns and capabilities can be studied.

In addition, the embodiments can be extended to study material pulmonary toxicity and the induced lung diseases such as lung cancer, asthma, bronchitis and emphysema, etc. The pulmonary toxicity is a function of material deposition in the lung. Thus, quantifying the material transported to the lung epithelium will provide the accurate prediction of pulmonary toxicity. Also, the embodiments may allow researchers to conduct age or gender related (e.g. children vs. adults and female vs. male) NM toxicity studies due to the easy 3D printing of patient-specific nose models.

Inhalation of aerospace materials, such as toluene, carbon nanotube can cause the development of brain diseases and lung cancer and other respiratory problems such as asthma, bronchitis and emphysema for the soldiers. It is not possible to currently perform the aerospace material toxicity studies on human beings. No realistic in vitro model is available today to predict the aerospace toxicant deposition in the brain lung, though limited data can be obtained by in vivo experiments which, however, require the sacrifice of animals. There is a pressing need for an approach to systematically assess the deposition of vast variety of aerospace material in the brain and lung and thus to provide basis for accurate prediction of the aerospace material brain and pulmonary toxicity.

As described, the embodiments of the present invention are related to a system, model and methods that are developed to simulate human inhalation toxicological screening or drug delivery of chemicals or materials. The embodiments include the use of fluidic channels (e.g. defined by a microfluidic system or biomaterial framework) mimicking the olfactory region in an artificial nasal cavity that allows the growth of olfactory neuron and/or epithelium cells. The anatomically correct human nasal cavity with the incorporation of human mucus plus neuron and/or epithelial cells allows the mimicking of real air flow to the human olfactory region via the nose.

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced items.

Thus, the scope of the invention should be determined by the appended claims and their legal equivalents, and not by the examples given.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An anatomical model of a nasal cavity, the model comprising:
   (a) a model body constructed of non-living material, the model body including upper and lower model portions configured to be affixed together to define the nasal cavity and including fluidic channels therein that define an olfactory region of the upper model portion and define a nasal passage of the lower model portion; and
   (b) a biocompatible porous membrane positioned between the upper and lower model portions when the upper and lower model portions are affixed together, the biocompatible porous membrane disposed adjacent the fluidic channels that define the olfactory region, wherein the membrane is configured for
      (i) culturing olfactory epithelium cells thereon and
      (ii) receiving particles that flow into the nasal cavity of the model body toward the fluidic channels that define the olfactory region;
   wherein the upper and lower model portions are configured to be separated and spaced from one another to enable access to the biocompatible membrane between the upper and lower model portions.

2. The anatomical model according to claim 1, further comprising an artificial mucous layer coating a surface of the nasal cavity and configured to collect particles passing through the nasal cavity.

3. The anatomical model according to claim 2, wherein the nasal cavity is configured to mimic the shape of a human nasal cavity.

4. The anatomical model according to claim 2, wherein the artificial mucous layer is configured to be removed after separation of the upper and lower model portions.

5. The anatomical model according to claim 1, wherein the upper and lower model portions comprise a silicone material.

6. The anatomical model according to claim 1, wherein the biocompatible porous membrane includes artificial pores defining the permeability of the biocompatible porous membrane.

7. The anatomical model according to claim 1, further comprising a microfluidic system defining the fluidic channels and configured for the growth of olfactory neuron and epithelium cells.

8. The anatomical model according to claim 1, further comprising a biomaterial framework defining the fluidic channels and configured for the growth of olfactory neuron and epithelium cells.

9. The anatomical model according to claim 1, further comprising a breathing system coupled to the model body and configured to simulate a breathing pattern with air entering and exiting via the nasal passage.

10. An anatomical model of a nasal cavity, the model comprising:
    (a) a model body constructed of silicone and including upper and lower model portions configured to be affixed together to define the nasal cavity and including fluidic channels therein that define an olfactory region of the upper model portion and define a nasal passage of the lower model portion; and
    (b) a biocompatible porous membrane positioned between the upper and lower model portions when the upper and lower model portions are affixed together, the biocompatible membrane configured for culturing olfactory epithelium cells thereon;
    wherein the upper and lower model portions are configured to separate to enable removal of the biocompatible membrane for analysis.

* * * * *